United States Patent [19]
Opperman

[11] Patent Number: 6,145,703
[45] Date of Patent: Nov. 14, 2000

[54] SPRAY APPLICATOR

[75] Inventor: Nicholas Richard James Opperman, Near Andover, United Kingdom

[73] Assignee: Pharmaso Limited, Andover, United Kingdom

[21] Appl. No.: 09/011,586

[22] PCT Filed: Aug. 16, 1996

[86] PCT No.: PCT/GB96/02011

§ 371 Date: Feb. 18, 1998

§ 102(e) Date: Feb. 18, 1998

[87] PCT Pub. No.: WO97/06842

PCT Pub. Date: Feb. 27, 1997

[30] Foreign Application Priority Data

Aug. 18, 1995 [GB] United Kingdom .................. 9516984

[51] Int. Cl.⁷ ........................................... B67D 5/00
[52] U.S. Cl. .................................. 222/82; 222/153.13
[58] Field of Search ............................. 222/82, 83, 83.5, 222/256, 153.13

[56] References Cited

U.S. PATENT DOCUMENTS

| | | |
|---|---|---|
| 4,083,428 | 4/1978 | Ness ........................................ 222/256 |
| 4,770,323 | 9/1988 | Debard . |
| 5,307,953 | 5/1994 | Regan ........................................ 222/83 |
| 5,503,302 | 4/1996 | DeJong ..................................... 222/82 |
| 5,509,578 | 4/1996 | Livingstone .............................. 222/82 |
| 5,518,147 | 5/1996 | Peterson et al. ................... 222/153.13 |

FOREIGN PATENT DOCUMENTS

| | | |
|---|---|---|
| 0531257 A1 | 5/1991 | European Pat. Off. . |
| 0569611 A1 | 5/1992 | European Pat. Off. . |
| 0546607 A1 | 6/1993 | European Pat. Off. . |
| 0679443 A1 | 11/1995 | European Pat. Off. . |
| 1436028 | 5/1976 | United Kingdom . |
| WO 95/00195 | 5/1995 | WIPO . |
| WO95/24972 | 9/1995 | WIPO . |

*Primary Examiner*—Andres Kashnikow
*Assistant Examiner*—Dinh Q. Nguyen
*Attorney, Agent, or Firm*—Wolf, Greenfield & Sacks, P.C.

[57] ABSTRACT

A multi-dose spray applicator is disclosed for dispensing a pharmaceutical liquid from a sealed container, said applicator comprising means for holding the container, a manually operable metering pump for delivering said pharmaceutical as a nasal spray, and a hollow needle associated with said pump for penetrating a membrane sealing said container and dispensing the pharmaceutical liquid through the pump, said container having a movable wall or plug which is movable to displace the liquid from the container as it is dispensed by the pump.

11 Claims, 7 Drawing Sheets

SPRAY APPLICATOR

BACKGROUND OF THE INVENTION

This invention relates to spray applicators, particularly for dispensing pharmaceutical substances. One established method of dispensing pharmaceuticals is by spray e.g as a nasal or oral spray. This method has the advantage as compared with sub-cutaneous or intravenal injection that it is easier for a patient with poor co-ordination or muscular weakness to administer the pharmaceutical himself. In the past, containers fitted with a pump or aerosol packaged products have been employed. However, these methods have proved to be unsatisfactory for packaging pharmaceuticals which are sensitive to substances in the atmosphere, such as compounds which degrade by contact with water or oxygen.

It is, therefore, one object of the present invention to provide an applicator for dispensing pharmaceuticals in the form of a spray, which minimises contact with atmospheric components until the product is dispensed.

SUMMARY OF THE INVENTION

WO 95/00195 discloses a spray applicator for dispensing a pharmaceutical from a sealed container, said applicator comprising means for holding said sealed container, a manually operable pump for delivering said pharmaceutical as a nasal spray and a hollow needle associated with said pump for penetrating a membrane sealing the container and dispensing the pharmaceutical through the pump. In accordance with the present invention, such a spray applicator is characterised in that the container has a moveable wall or plug which is movable to displace liquid from the container as it is dispensed by the pump. An advantage of the invention is that liquid from within the container can be displaced without the need to introduce air or other gas into the sealed container.

The applicator of the present invention is particularly designed for dispensing pharmaceuticals which are sensitive to oxygen or water. One example of such a compound is apomorphine hydrochloride (or other pharmaceutically acceptable salt) which is widely used in the treatment of Parkinson's disease. For such use, apomorphine is conveniently applied as a nasal spray and is rapidly absorbed through the nasal membrane. The spray applicator may, however, be adapted for other purposes, e.g. for applying a spray to the mouth and for dispensing other pharmaceuticals via the mouth or nose, particularly for treating the mouth, nose and lungs.

The pump component of the applicator may be constructed as a metering pump so that on actuation of the pump, a metered dose of the pharmaceutical is sprayed into the patient's nose or mouth.

Preferably, the applicator includes means for moving the needle towards the membrane automatically on actuation or just prior to actuation of the pump. For example, depression of the pump system may cause the needle to move towards and penetrate a membrane sealing the container in which the pharmaceutical is packaged.

In order to prevent the device from being actuated unintentionally, the applicator may include a removable device such as a clip, ring or tag which prevents the needle penetrating the membrane or prevents, respectively, means carrying the needle and sealed container from coming together until the applicator is intended to be used.

When the needle penetrates the membrane over the end of the vial, the contents remain substantially sealed with respect to the atmosphere so that air cannot enter the vial.

The moveable wall or plug may be urged inwardly by a spring or other mechanical. device so as to assist prig the pump, although the spring is not essential. The container may be constructed as a collapsible container, such as a tube, by making the walls from a flexible material such as a plastics sheet material.

One pharmaceutical application of the spray applicator is for dispensing compounds for controlling Parkinson's Disease. Patients suffering from Parkinson's Disease often have difficulty in manipulating deices for administering their medication. A further feature of the applicator of the invention is to provide a dispensing cap in which the outlet from the pump is angled obliquely, thus providing a platform on the cap of the applicator which enables the patient to operate the pump conveniently with his thumb.

Two embodiments of the present invention will now be described with reference to the accompanying drawings, which are partly schematic.

Referring to FIGS. 1 to 4 of the accompanying drawings, the nasal applicator comprises a container (1) shaped to receive a sealed vial (2) into which the pharmaceutical is packaged. Vial (2) is of a type which is currently used in the pharmaceutical industry for packaging injectable materials. The vial comprises a glass or plastics tube (3) having a lower end which is closed with a rubber or plastic bung or plug (4). The upper end of the vial has membrane (5) which is designed to be penetrated by a hypodermic needle for removing the contents. After penetration of the membrane the membrane is sufficiently elastic to close around the needle and seal itself against inadvertent escape of liquid or escape under the pressure arising during pumping of doses of liquid from the container. The membrane is preferably a rubber or rubbery plastics material. Vial (2) is designed to be a multi-dose container so that as liquid is removed from the vial (2), plug (4) moves upwardly to displace the liquid so removed. A spring (6) may be employed to assist this action and/or priming of the pump but is not essential. At its upper end, container (1) is threaded to receive a cap (7) and a pump holder (8) is mounted for axial sliding movement on the neck (9) of the container (1). Crimped onto the neck (10) of the pump holder (8) is a pump (11) and mounted on the upper end of the pump is a nasal actuator and overcap (12) and (13) respectively. Pump (11) is of the kind conventionally used for pumping pharmaceuticals from closed containers. The pump may be an airless mechanical pump with or without a dosing device such as those manufactured by Perfect-Valois or their parent company Valois Step under model No. 'VP 7'. An example of a metering pump of this kind is also described in WO 95/09054.

Figure 1:
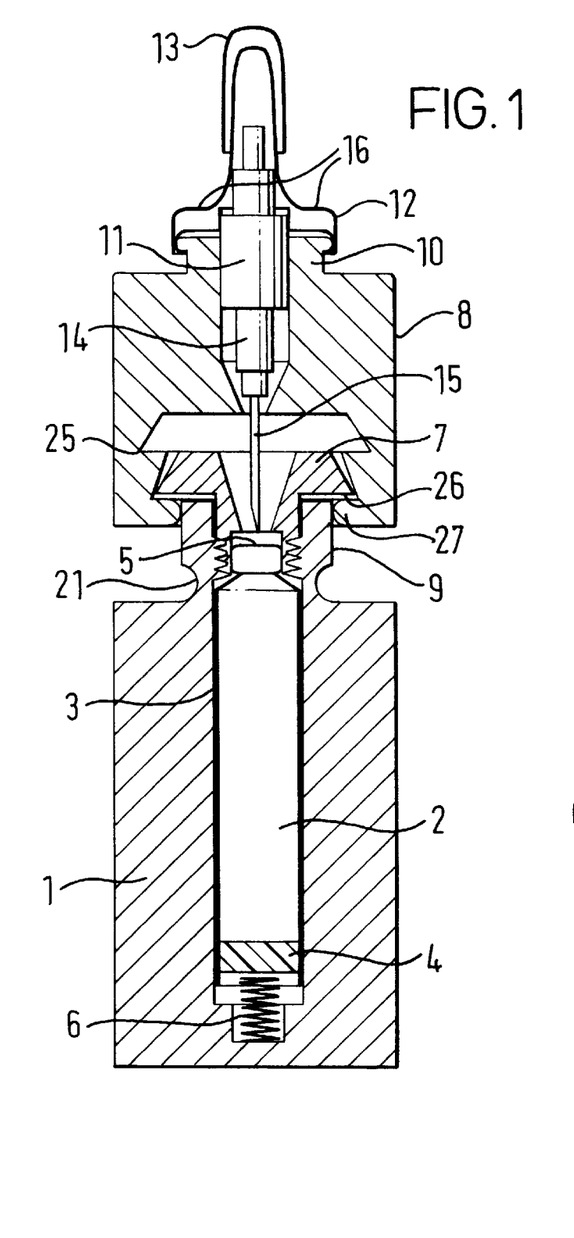
FIG. 1 is a longitudinal section through the applicator in assembled condition.

The lower end of the pump (11) has a tubular portion (14) to which a hollow needle (15) is attached either internally or externally, e.g. by means of a luer-type connection.

The applicator works in the following manner. Cap (13) which is a press fit of actuator (12) is removed and the actuator pressed down by placing the fingers on ledges (16). This causes pump holder (8) to move downwardly until needle (15) penetrates the membrane (5) and enters the liquid contained in vial (2). Continuing downward pressure causes the pump to take in a dose of the pharmaceutical and to spray the dose through the nasal actuator (12). On release of such finger pressure, needle (15) remains in the vial with the membrane sealing around the needle to prevent escape of liquid between the outer surface of the needle and the membrane. This is because the underside 26 of the cap engages with the recess 25 of the cap 8 or the annular projection 27 engages in the groove 21. The piston (not shown) within pump 11 is returned to its initial position by a return sprig within the pump housing 11. This aspirates liquid into the pump ready for dispensing the next dose from the vial. Further doses of liquid can be pumped from the vial by the patient as required by pressing on the ledges 16.

Figure 2:
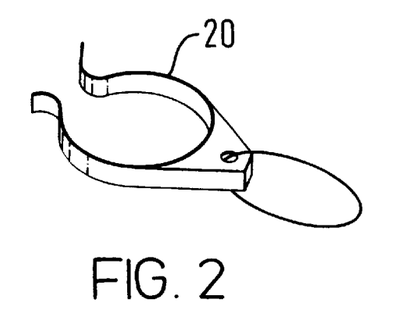
FIG. 2 is a perspective view of a clip for preventing the needle penetrating the sealed container.
Figure 3:
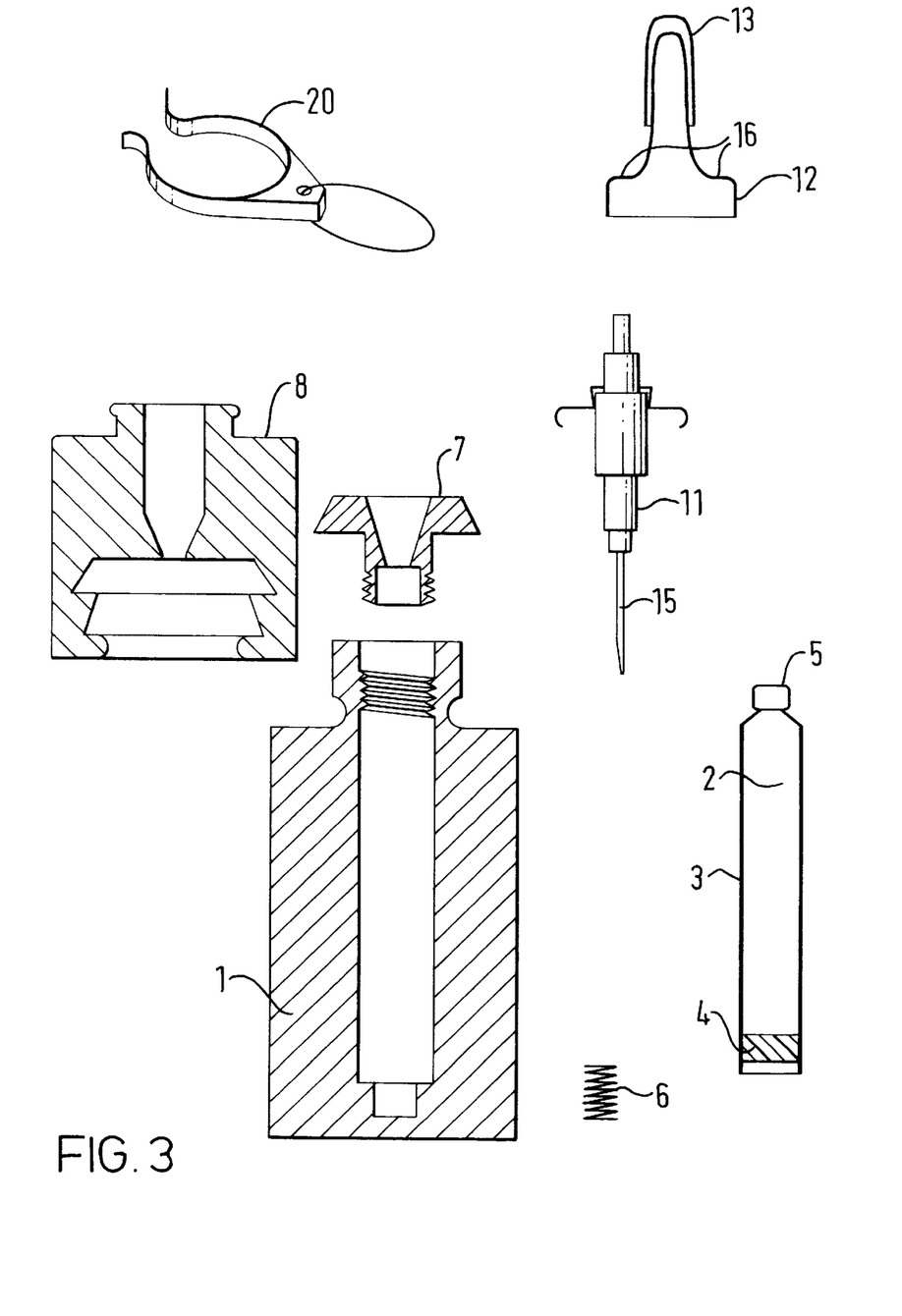
FIG. 3 shows the components of the applicator in a disassembled state.

In order to prevent the applicator from being inadvertently actuated, a removable clip (20) may be fitted into a groove (21) in the neck (9) of container (1). The clip (20) may be manufactured from a springy plastics material so that it is readily removed by puling the tag or ring which is attached to it. When the clip (20) is in place, however, its thickness or an abutment protruding from it, prevents the pump holder moving down the neck (9) sufficiently far to allow the hollow needle to penetrate the membrane (5).

Figure 4:
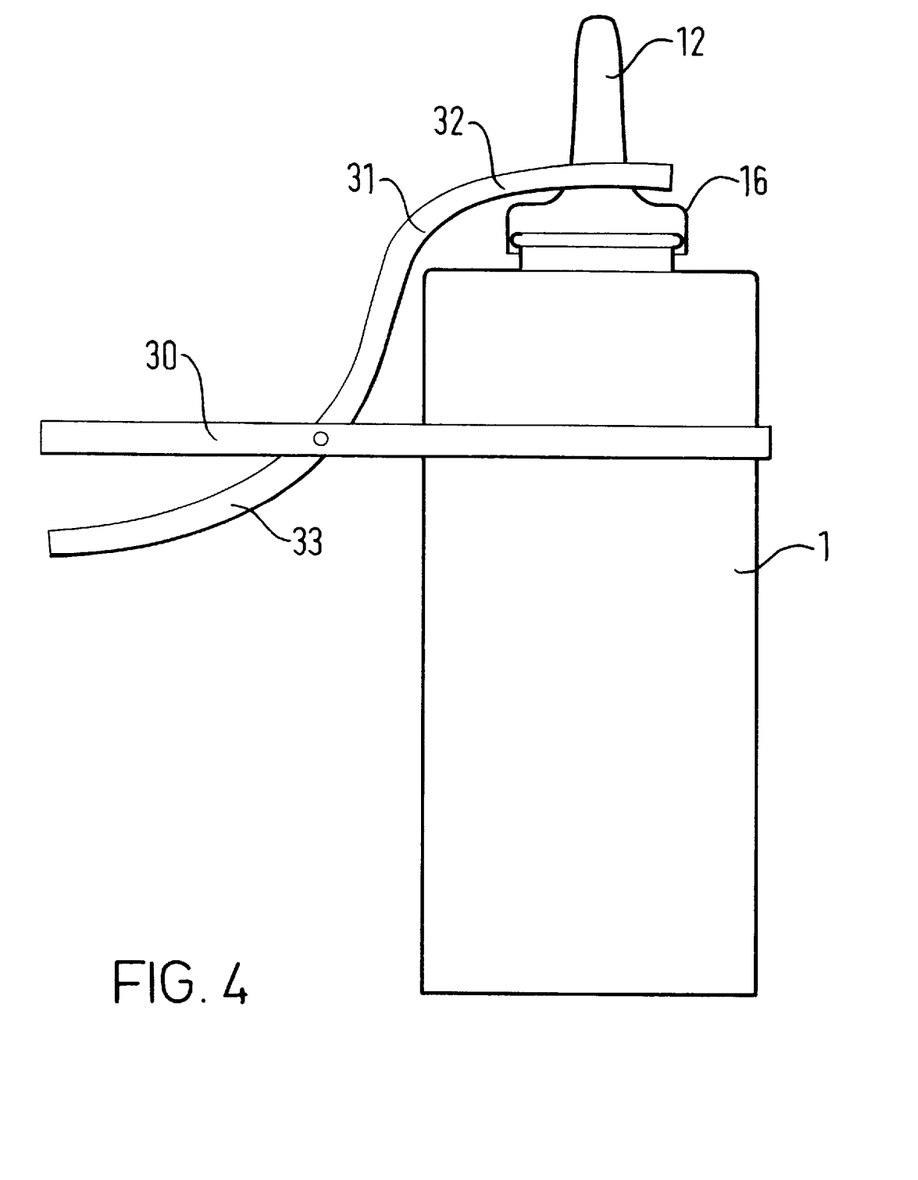
FIG. 4 is a schematic view showing an alternative method of actuating the pump.

FIG. 4 shows an alternative way of depressing the actuator (12) for patients who have very poor co-ordination or muscular power. In this modification, the container (1) may be gripped by a holder (30) having a lever (31) mounted thereon. Lever (31) has an arm (32) which is shaped to press onto shoulders (16) of the nasal actuator (12). By operating lever arm (33), the patient is able to actuate the applicator with minimum mechanical force.

It will be appreciated that various modifications can be made to the applicator in accordance with the invention. For example, the holder may be formed with a threaded, removable base for introducing the vial and the neck (7) may be formed integrally with the body (1). The pump unit may be crimped downwardly onto the neck of the holder and be arranged to be movable downwardly to permit the needle to enter the membrane (5).

Conveniently, most of the components of the applicator may be manufactured from plastic materials. The holder (1) may, for example, be made from a clear plastics material so that the patient can see whether the vial is empty. In the case of apomorphine, the pharmaceutical turns green after exposure to atmospheric oxygen. Once the components of the vial are observed to have changed to a green colour which is sufficiently deep (as indicated by a shade chart on the applicator or packaging), to indicate that the pharmaceutical is no longer effective. An important aspect of the application of this invention is that the pharmaceutical in the vial remains sealed from the atmosphere until the patient uses the applicator for the first time.

FIGS. 5, 6, 7, 8A & 8B show modified applicators which include a number of modifications but work in a similar fashion to the applicator shown in FIGS. 1 to 4.

Figure 5:
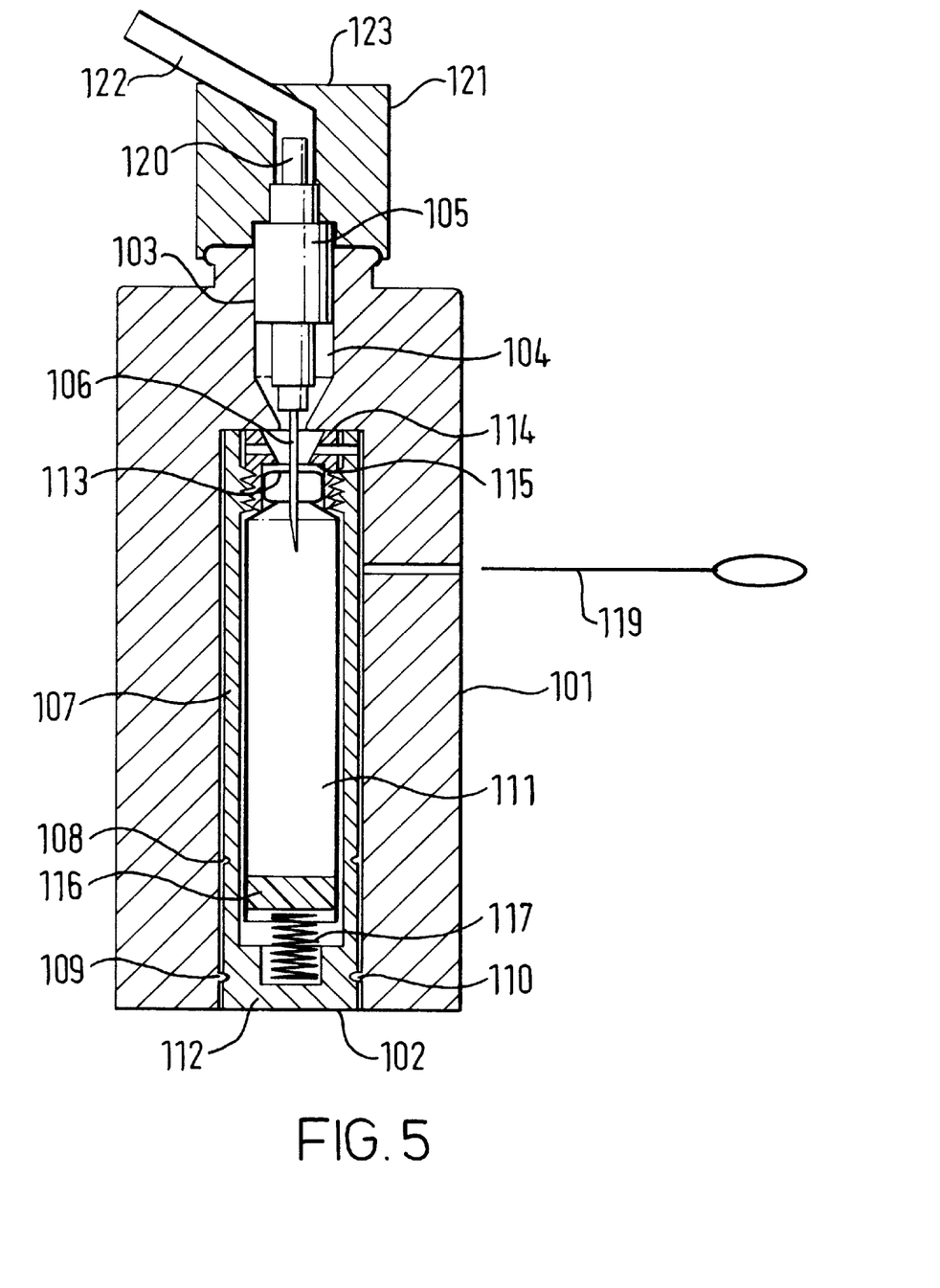
FIG. 5 is a longitudinal view in section of a second embodiment of the applicator in its "use" position.
Figure 6:
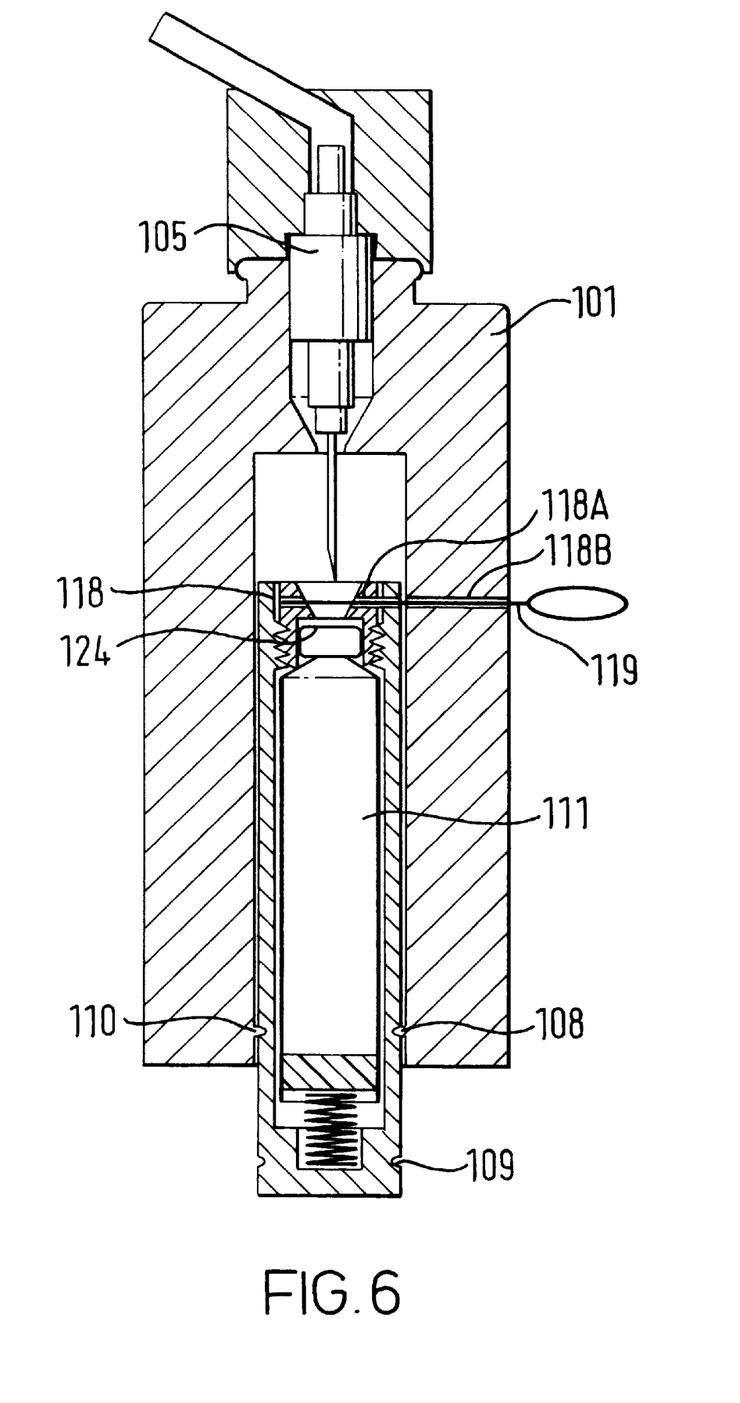
FIG. 6 is a similar section through the applicator shown in FIG. 5. but in its "rest" position.
Figure 7:
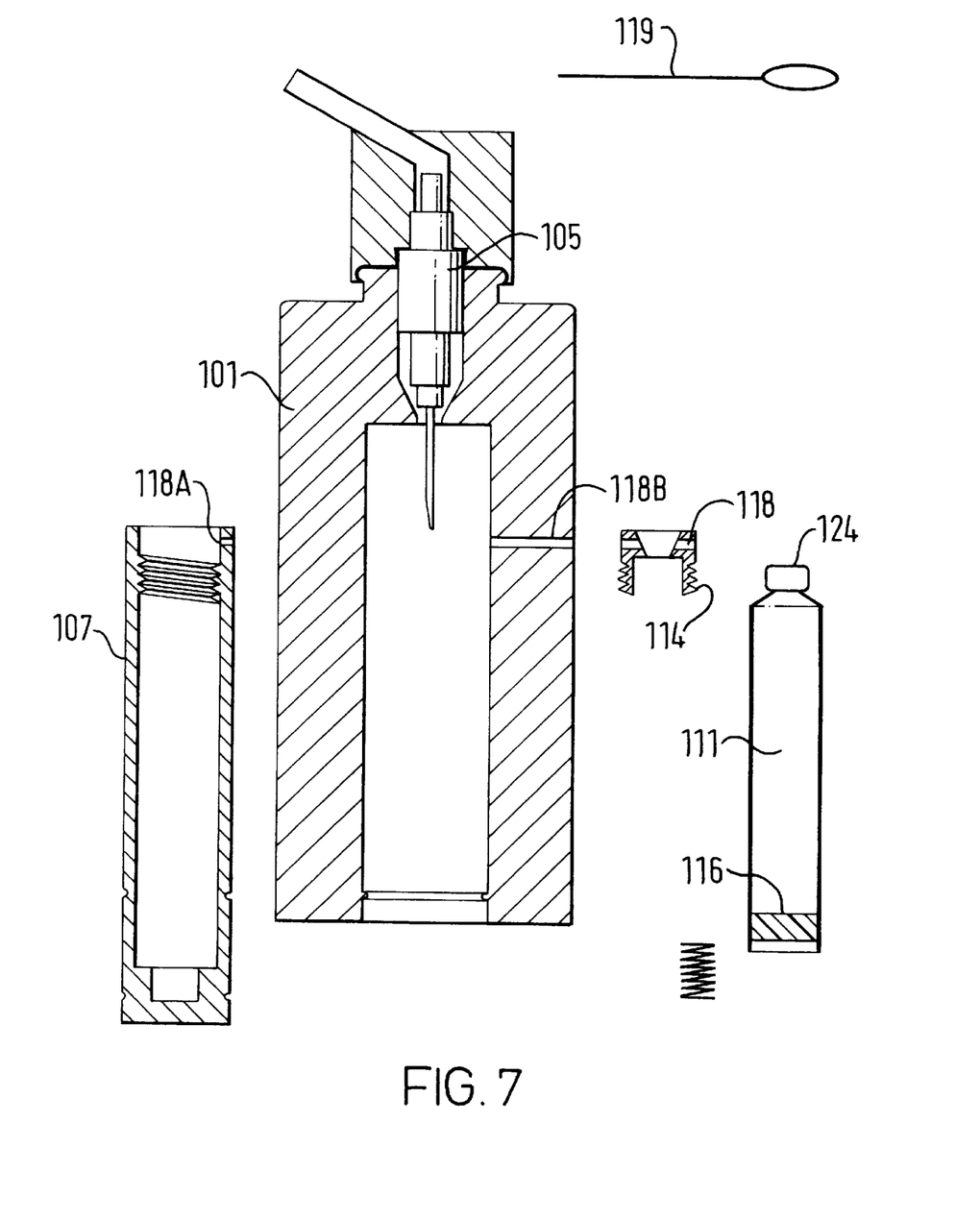
FIG. 7 shows the disassembled components of the applicator shown in FIGS. 5 and 6.
Figure 8A:
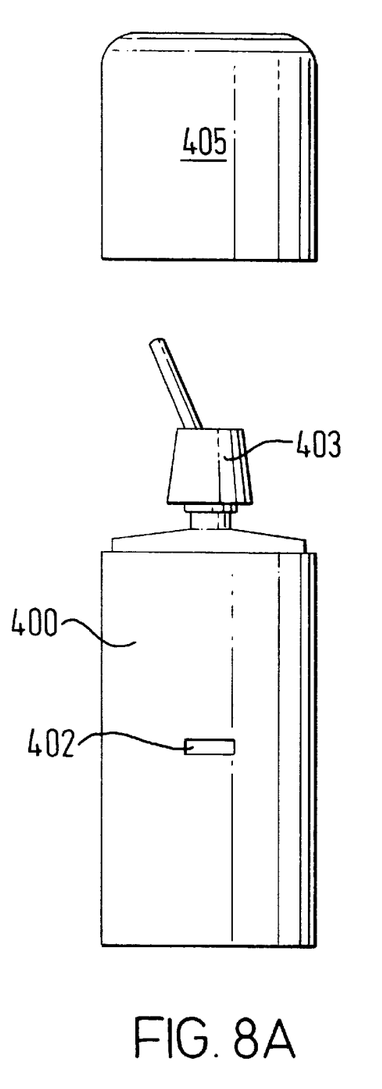
FIGS. 8A and 8B are two perspective views of a modified dispenser.
Figure 8B:
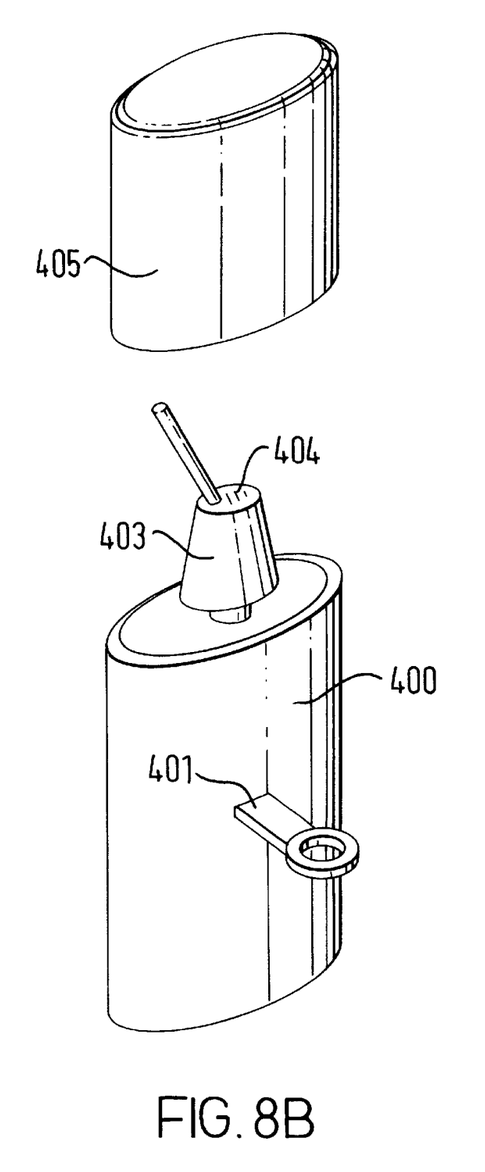

Referring to FIGS. 5, 6 and 7, the modified dispenser comprises an outer hollow component (101) forming one part of a container, preferably moulded from plastics material. In the embodiment shown in these Figures, the pump (105) is the same kind of metering pump as already described in connection with FIGS. 1 to 4. Also, the vial (111) is essentially as described in relation to the embodiments of FIGS. 1 to 4. The differences concern the container for the vial and the nozzle through which the product is dispensed. Component (101) is open at one end (102) and at its other end (103) is formed with a mouth and throat (104) for receiving a dosing pump (105). Pump (105) is preferably crimped into the mouth (104) of component (101), e.g. with an aluminium closure ferrule. A hollow needle (106) is fitted to the pump (105).

A second component (107) of the container is slidably received in the tubular hollow part of component (101). Again the second component is conveniently moulded from plastics material. Component (107) is formed with two longitudinally spaced grooves (108) and (109) and the inside of the component (101) is formed with a corresponding annular ring or projection (110).

Component (107) is formed with a tubular cavity for receiving a vial (111) and has a closed base (112) and a neck (113). Vial (111) is retained within the component (107) by a threaded cap (114) which engages with corresponding threads on the inside of the neck of the component (107). Alternatively, the cap (114) may be a friction fit in the neck of component (107) or one of the components may have lug(s) which engage with groove(s) or recesses. In use, the shoulder of the vial (111) will abut against the cap (114) or the neck will abut against a ledge (115). However, for clarity a slight gap is shown in the drawing. Vial (111) is a tube open at its lower end but includes a sealing plug (116) (preferably of elastomeric material). Plug (116) is preferably in contact with a spring (117) tending to urge the plug towards the neck of the vial As shown in FIG. 6. the cap (114) is formed with a slot (118) into which a guard strip (119) slides. Guard strip (119) passes through slots (118A & 118B) in components (101 & 107) which are aligned with slots (118) in cap (114). The width and toughness of sip (119) is such that it would be difficult for needle (106) to penetrate it and reach the membrane across the neck of vial (111).

Pump (105) has an outlet tube (120) depression of which causes the pump to operate. Tube (120) is received within a nasal spray head (121) which has a dispensing nozzle (122) connected to the tube (120). Nozzle (122) extends obliquely to the centre line of the dispenser so as to provide a convenient ledge (123) for the patient to apply finger pressure to operate the device.

The dispenser shown in FIGS. 5, 6 and 7 works in the following manner. In the position shown in FIG. 6. the projection (110) engages in groove (108) and releasably retains the inner component in relation to the outer component (101) in the position shown in FIG. 6.

When it is desired to use the dispenser, the guard strip (119) is pulled out by puling on the ring. The dispenser can then be operated by pressing the base (112) on a flat surface and pressing, e.g. with the thumb on the ledge (123). This causes the inner component to be pressed into the outer component (101) and the needle to penetrate the membrane (124) across the neck of the vial. At the same time, the annular projection (110) engages in the groove (109) thus retaining the component (107) within the component (101). For this purpose, projection (110) can be made to be a better fit in groove (109) than in groove (108) so that it is easier to dislodge projection (110) from groove (108) than groove (109).

It has been found that a needle which has a very slight or no taper at all is best employed. This is because needles with a long taper tend to allow the contents of the vial to spray out as the needle begins to penetrate the membrane. However, conventional needles may be employed.

The walls of the components (101,107) may be transparent or include a window. This arrangement enables the contents of the vial to be checked e.g. to see if the vial contains sufficient liquid for one more treatment or, in the case of some medicaments, to check the appearance of the contents since this can undergo a colour change which may indicate it is no longer effective.

Instead of having a sprig such as the spring (6) shown in the embodiments of FIGS. 1 to 3, a projection is moulded on the base (108). This projection bears on the plug (112) so that when the applicator is initially activated, the plug is urged upwardly and primes the pump.

FIGS. 8A and 8B show external perspective views of a modified dispenser. In this embodiment, the vial (not visible) is contained within a body 400 which may be formed from inner and outer components similar to components (101, 107) in FIGS. 5 and 6. A guard sip (401) is received in a slot (402) and prevents the dispenser being actuated inadvertently. A spray head (403) is fitted to the discharge tube of the pump and provides a platform (404) for applying finger or thumb pressure to operate the pump. Nozzle (405) terminates in a discharge outlet which may incorporate various outlet designs to vary the spray pattern. A closure cap (405) may be fitted over the nozzle to protect the nozzle for storage and transport.

What is claimed is:

1. A multi-dose spray applicator for dispensing a pharmaceutical liquid from a sealed container, said applicator comprising a holder for the container, a manually operable metering pump for delivering said pharmaceutical liquid as a nasal spray and a hollow needle associated with said pump for penetrating a membrane sealing said container and dispensing the pharmaceutical liquid through the pump, wherein said container has a movable wall or plug which is movable to displace the pharmaceutical liquid from the container in response to the action of the pump as the liquid is dispensed by the pump.

2. An applicator as claimed in claim 1, which includes means for moving the needle towards the membrane on initial actuation of the pump.

3. An applicator as claimed in claim 2, which includes a removable safety device to prevent the needle penetrating the membrane until the applicator is intended to be used.

4. An applicator as claimed in claim 3 in which the safety device comprises a shield located between the membrane and the needle, said shield being movable to an inoperative position when the applicator is intended to be used.

5. An applicator as claimed in claim 3 in which the safety device comprises a locking means which in its operative position prevents a component carrying the pump from moving towards the container to an extent that the needle penetrates the membrane.

6. An applicator as claimed in claim 1, wherein the plug is movable into the container under the influence of a spring.

7. An applicator as claimed in claim 1 in which the pump is primed by movement of the needle into the container.

8. An applicator as claimed in claim 1, wherein the means for holding the container comprises a housing, said housing comprising a base part for holding said container and a top part for holding the pump, the top and base parts being relatively movable to allow the needle to penetrate the membrane.

9. An applicator as claimed in claim 8, wherein the base part is slidable within the top part and the two parts are cooperatively held together with the end of the needle within the container and the membrane forming a seal around the needle.

10. An applicator as claimed in claim 9, wherein the two parts are cooperatively held together with one resilient finger on one part which is engageable in a recess in the other part.

11. An applicator as claimed in claim 1 in which the container walls are flexible and collapse as the pharmaceutical liquid is dispensed by the pump.

* * * * *